US006727204B1

(12) United States Patent
Bergeron et al.

(10) Patent No.: US 6,727,204 B1
(45) Date of Patent: Apr. 27, 2004

(54) USE OF CROSSLINKED POLYMERS AS ANTI-LEACHING AGENTS

(75) Inventors: Vance Bergeron, Anthony (FR); Cécile Bonnet-Gonnet, Paris (FR); Jean-Christophe Castaing, Paris (FR); Giles Guerin, Eaubonne (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/936,860

(22) PCT Filed: Mar. 17, 2000

(86) PCT No.: PCT/FR00/00661

§ 371 (c)(1),
(2), (4) Date: Jan. 7, 2002

(87) PCT Pub. No.: WO00/56147

PCT Pub. Date: Sep. 28, 2000

(30) Foreign Application Priority Data

Mar. 19, 1999 (FR) .............................................. 99 03454

(51) Int. Cl.$^7$ .............................................. A01N 25/24
(52) U.S. Cl. ....................... 504/113; 504/362; 424/484; 424/485; 424/488; 514/769; 514/781; 514/782
(58) Field of Search ................................. 504/113, 362; 424/485, 488, 484; 514/769, 781, 782

(56) References Cited

U.S. PATENT DOCUMENTS

| 4,110,431 A | 8/1978 | Oita ............................ 424/78 |
| 4,123,429 A | 10/1978 | Brouard ........................ 71/66 |
| 4,401,456 A | 8/1983 | Connick ........................ 71/88 |
| 5,077,314 A | 12/1991 | Philips ....................... 514/640 |

FOREIGN PATENT DOCUMENTS

| CA | 761872 | 6/1967 | ..................... 71/13 |
| DE | 281 109 A5 | 4/1989 | .......... A01N/25/10 |

*Primary Examiner*—S. Mark Clardy

(57) ABSTRACT

The invention concerns the use, in an aqueous spray mixture comprising a phytosanitary formulation, of an anti-leaching agent comprising: at least a polyhydroxyl and/or polycarboxyl polymer or copolymer; at least a crosslinking agent comprising a metal selected among columns IVA, IB and IIIB of the periodic table; said anti-leaching agent being, in the aqueous spray mixture, in the form of an aqueous solution or dispersion having a polymer or copolymer concentration such that the viscosity of the anti-leaching agent is not more than 10 times the viscosity of the aqueous solution in polymer or copolymer without crosslinking agent, having the same concentration.

18 Claims, No Drawings

USE OF CROSSLINKED POLYMERS AS ANTI-LEACHING AGENTS

This application is an application under 35 U.S.C. Section 371 of International Application Number PCT/FR00/00661 filed on Mar. 17, 2000.

The present invention relates to the use, in aqueous atomizing sprays comprising a phytosanitary formulation, of an anti-leaching agent which comprises at least one polyhydroxylated and/or polycarboxylated polymer or copolymer, and at least one reticulating agent comprising a metal.

The present invention relates more particularly to the sphere of phytosanitary formulations, comprising pesticides or agents controlling the growth of plants.

Moreover, the present invention concerns the sphere of phytosanitary formulations intended to be applied to the plants to be treated, in the form of a solution, dispersion or emulsion in an aqueous medium. It should be noted that for the sake of simplicity of the preamble, in the following description, reference will be made only to aqueous solutions, knowing that this term encompasses the above-mentioned variants.

The phytosanitary formulations utilized in the form of an aqueous solution are conventionally sprayed onto the plant to be treated. One of the main difficulties encountered with this method of use lies in the fact that it is difficult to keep the active ingredient on the plant. This is because, with the first rain or morning dew, the film deposited on the plant swells up again in the presence of water and the active ingredient is washed away with the water, which considerably reduces its efficacy.

The present invention relates to the use of an aqueous atomizing spray comprising a phytosanitary formulation and a special anti-leaching agent. The latter is present, while the spray is being utilized, in the form of a low-viscosity solution or dispersion. Consequently, the resultant spray can easily be pumped and atomized. Moreover, the anti-leaching agent, whilst drying on the plant being treated, forms a gel, considerably limiting the leaching of the active ingredient applied. It should be noted that, completely advantageously, the gel does not form during the preparation or use of the spray, nor during preparation of the phytosanitary formulation if it contains the anti-leaching agent, but only while the spray is drying on the plant treated.

Thus, the present invention consists in the use, in an aqueous atomizing spray comprising a phytosanitary formulation, of an anti-leaching agent comprising:

at least one polyhydroxylated and/or carboxylated polymer or copolymer, at least one reticulating agent comprising at least one metal selected throughout from Columns IVA, IB and IIIB of the periodic table of the elements, said anti-leaching agent being present, in the aqueous atomizing spray, in the form of an aqueous solution or dispersion with a polymer or copolymer concentration such that the viscosity of the anti-leaching agent is less than or equal to 10 times the viscosity of an aqueous polymer or copolymer solution free from reticulating agent having the same concentration.

The anti-leaching agent present in the atomizing spray, once applied to the plant and dried, forms a reticulated film which swells only slightly in the presence of water. The film containing the active material therefore retains better cohesion to the surface on which it is formed, thus considerably increasing the efficacy of the active ingredient.

The anti-leaching agent according to the invention, moreover, has other very important advantages, such as that of avoiding losses of active ingredients during spraying. This is because the anti-leaching agent reduces the phenomena of the atomized droplets being carried away by the wind (anti-drift), and also that of their rebounding when they come into contact with the hydrophobic surface of the plant to be treated.

It should also be noted that the anti-leaching agent may be present in different forms. Thus it can be present in solid form, or else in the form of a dispersion in a compound which is not a polymer or copolymer solvent, such as oils.

Moreover, the anti-leaching agents can be utilized as a phytosanitary formulation additive. In other words, the anti-leaching agent is mixed with the phytosanitary formulation during use of the latter; the whole producing the aqueous atomizing spray.

It is likewise possible to utilize phytosanitary formulations comprising the anti-leaching agent. In this case, the anti-leaching agent is said to be used as a constituent of the phytosanitary formulation.

It should be noted that under the conditions described, the anti-leaching agent and optionally the phyosanitary formulation containing it are stable in storage and no appearance of non-manipulable gel is observed. In addition, the aqueous spray comprising the phytosanitary formulation and the anti-leaching agent is also stable.

However other advantages and characteristics of the present invention will become clearer on reading the description which follows.

The anti-leaching agent will first be described in detail.

As indicated above, the anti-leaching agent comprises at least one polyhydroxylated or polycarboxylated polymer and/or copolymer.

The polymer or copolymer is preferably present in soluble form in aqueous media.

According to a first variant, the polyhydroxylated polymer or copolymer is selected throughout from polysaccharides of animal, plant or bacterial origin, cellulose derivatives or polyvinyl alcohol, polyphenolic alcohol or their derivatives, as well as glycol polyoxalkylene derivatives.

The polysaccharides can be used in native form or chemically modified to give them an ionic, non-ionic and/or hydrophobic character different from that of the native form.

The following may be cited as examples of polysaccharides, without this list being exhaustive: alginates, galactomannanes such as guar gum, carob gum, Tara gum, cassia gum, Karaya gum, carragheenans, chitin derivatives such as chitosan, amidones, glucomannanes, dextran, gum arabic, soluble amidone and its non-ionic (cationic) derivatives. The derivatives of these alkylated compounds are also suitable.

Of the cellulose derivatives that may be included within the present invention, mention may be made in particular of cellulose derivatives such as cellulose hydroxyethers, methyl cellulose and its derivatives, hydroxypropylmethyl cellulose, hydroxybutylmethyl cellulose, carboxymethyl cellulose, ethylmethyl cellulose, ethyl cellulose, hydroxyethyl cellulose, hydroxypropyl cellulose, as well as other hydroxyaklylated derivatives of cellulose generally.

The following can be cited as suitable derivatives of guar: compounds resulting from an etherification and/or esterification reaction, such as hydroxyalkyl guars (with the alkyl radical comprising 2 to 4 carbon atoms, linear or branched), such as hydroxypropyl guar, hydroxybutyl guar; such as carboxymethyl guar; such as carboxymethyl hydroxalkyl guars (with the alkyl radical comprising 2 to 4 carbon atoms, linear or branched). Also suitable are cationic compounds of guar, carrying quaternary amine groups. Finally, alkylated compounds of guar and of the abovementioned derivatives can be utilized in the invention.

As biogums that can be utilized in the anti-leaching agent, mention may be made in particular of the polysaccharides obtained by fermentation by the action of bacteria or funghi belonging, for example, to the Xanthomonas, to the genus Arthrobacter, the genus Azobacter, the genus Agrobacter, the genus Alcaligenes, the genus Rhizobium, the genus Sclerotium, the genus Corticium and the genus Sclerotinia.

As examples of biogums, mention can be made more particularly of xanthan gum, the scleroglutanes, and the succinoglycanes.

As polyhydroxylated polymers or copolymers, and as indicated above, the following are suitable: polyvinylic alcohol, the polyphenolic alcohols or their derivatives.

The possible derivatives include the polyetherified (co) polymers, such as those whose ether part is an alkyl radical in $C_1$–$C_{18}$, or an aryl radical in $C_6$–$C_{16}$, or an alkylaryl or arylalkyl radical; the alkyl and aryl parts being defined above.

Further derivatives that may be suitable are (co)polymers carrying at least one ionic (anionic, cationic, zwitterionic, amphoteric) radical. The following list, which is not intended to be exhaustive, includes anionic radicals: sulphonate-, sulphate-, carboxylate-, phosphate-, phosphonate-type radicals; examples of cationic radicals include quaternary ammonium-type radicals as —$N(R_3)+$, with R, identical or different, representing a hydrogen atom, and an alkyl radical in $C_1$–$C_6$; the zwitterionic and amphoteric radicals corresponding to a combination of the two abovementioned types of radicals.

It is noted that the polyphenolic-type (co)polymers are natural substances which can, in particular, be extracted from certain plants such as coffee plants and tea bushes.

Another type of polyhydroxylated polymer or copolymer corresponds to the polyolxyalkylenated derivatives of glycol, the alkylene oxide part corresponding to ethylene oxide, propylene oxide or mixtures of these. In the case of ethylene oxide and propylene oxide being present, their distribution may be statistical or block. A polyoxyethylenated glycol derivative is preferably utilized.

According to a preferred variant of the invention, the polyhydroxylated polymer or copolymer is selected throughout from guar gum and its non-ionic, anionic, cationic, and amphoteric derivatives. More particularly, use is made of guar, optionally alkylated, hydroxyalkyl guars (with the alkyl radical comprising 2 to 4 carbon atoms, linear or branched); carboxymethyl guar; carboxymethyl hydroxyalkyl guars (with the alkyl radical comprising 2 to 4 carbon atoms, linear or branched) and their alkylated derivatives. In the same way, cellulose and its derivatives such as, notably, carboxymethyl cellulose, are preferred polyhydroxylated polymers or copolymers.

Suitable polycarboxylated polymers or copolymers are those obtained from:
- at least one saturated or non-saturated monomer, comprising 3 to 10 carbon atoms and comprising one or more carboxylic groups present in the form of acid, or of alkaline metal salts,
- optionally combined with at least one hydrocarbonated monomer carrying one or more ethylenic non-saturations; or
- optionally combined with at least one alkylene-oxide-type monomer. As saturated or non-saturated monomers comprising one or more carboxylic groups and comprising 3 to 10 carbon atoms, mention may be made of the mono- or di-acids, and their derivatives in the form of alkaline metal, alkaline-earth or ammonium salts (type $N(R)_4+$, with R representing hydrogen or an alkyl radical in $C_1$–$C_4$.

For example, mention may be made of acrylic acid, methacrylic acid, itaconic acid, maleic acid, maleic anhydride, and fumaric acid.

Amino-acids or their salts, e.g. aspartic acid, may likewise be suitable for carrying out the invention.

As regards the hydrocarbonated monomer, mention can be made, without intending to be restrictive, of the hydrocarbonated monomers in $C_2$–$C_{12}$, which may or may not comprise an aryl radical, and also have at least one ethylenic non-saturation. The following, amongst others, are suitable: butadiene, isobutylene, duisobutylene, styrene, vinylstyrene, alphamethylstyrene and vinyl toluene.

In relation to the alkylene-oxide-type monomer, mention may be made of ethylene oxide, propylene oxide or mixtures of these.

The anti-leaching agent may comprise one or more of the polymers or copolymers just described.

Moreover, the polymer or copolymer utilized in the anti-leaching agent has, more particularly, a molecular mass by weight between $10^4$ and $5.10^6$ g/mol. The molecular mass of the compound is preferably between $5.10^5$ and $5.10^6$ g/mol, and according to one particular variant between $10^6$ and $5.10^6$ g/mol.

These masses are measured either by chromatography by steric exclusion or by quasi-elastic diffusion of the light.

The anti-leaching agent comprises, in addition, a reticulating agent containing at least one metal selected throughout from Columns IVA, IB and IIIB of the periodic table of the elements (the table referred to is that published in the supplement to the Bulletin de la Société Chimique de France no. 1 of January 1966).

More particularly, boron is not present. The preferred metals are titanium, zirconium, copper, and aluminium. These metals can be utilized alone or in combination.

The reticulating agent included in the anti-leaching agent is present, more particularly, in the form of a water-soluble, water-dispersable or emulsifiable compound.

According to a first possibility, the reticulating agent is present in the form of organic derivatives selected throughout from linear or branched, saturated or non-saturated carboxylic or aliphatic acid salts comprising 2 to 18 carbon atoms, and optionally comprising one or more hydroxylated groups.

For example, acetic, citric, lactic, oleic, stearic and myristoloeic acid salts are suitable.

Another variant consists in utilizing the reticulating agent in the form of aliphatic-diketone or -ketoester chelates comprising 5 to 10 carbon atoms, or comprising at least one aromatic radical.

Of the suitable compounds of this type, mention may be made of the chelates of acetyl acetone, methyl acetyl acetonate, ethyl acetyl acetonate, benzoyl acetone, dibenzoyl methane, heptanoyl benzoyl methane, octanoyl benzoyl methane, isooctanoyl benzoyl methane, nonanoyl benzoyl methane, and stearoyl benzoyl methane.

According to a second possibility, the reticulating agent is utilized in the form of mineral derivatives selected throughout from oxides, hydroxides or derivatives of these.

It should be noted that the reticulating agent can be utilized in a form that is not, or that is only slightly, soluble in an aqueous medium. In this case, it will be present, when the anti-leaching agent is utilized, in the form of a dispersion, an emulsion, or a micro-emulsion.

In such a case, and in order best to promote its homogeneous dispersion within the aqueous atomizing spray, the reticulating agent is preferably used in a finely divided form. More particularly the average size of the particles is smaller than one micron and preferably less than 200 nm. It should be noted that the term "particles" encompasses not only the reticulating agents present in solid form, but also in liquid form, or both.

According to one particular embodiment of the invention, the reticulating agent, if it is not, or if it is only slightly, soluble in an aqueous medium, can be utilized with an appropriate amphiphilic (dispersant, surfactant) compound, improving the homogeneous distribution of said reticulating agent during use of the anti-leaching agent.

Highly advantageous reticulating agents suitable for the invention include zirconium lactate, zirconium citrate, zirconium acetyl acetonate, zirconium acetate, titanium oxide and aluminium oxide.

The weight ratio of the reticulating agent and the polymer or copolymer is more particularly between 0.005 and 2, and preferably between 0.01 and 0.5.

It should be noted that the choice of constituents of the anti-leaching agent depends on the pH of the aqueous phase of the atomizing spray. Said constituents are preferably selected throughout so that they do not form a precipitate under the pH conditions to which they are subjected during preparation and use of said anti-leaching agent.

As indicated above, the reticulating agent, in the aqueous pulverizing spray, is present in the form of an aqueous solution or dispersion having a polymer or copolymer concentration such that the viscosity of the anti-leaching agent is less than or equal to 10 times the viscosity of an aqueous polymer or copolymer solution free from reticulating agent having the same concentration.

Under these conditions, and despite the presence of the two consituents of the anti-leaching agent, the atomizing spray has a viscosity that makes pumping and atomizing operations simple. In addition, the spray is stable.

The spray solvent is preferably water. However, replacing the water by a mixture of alcohol or polyalcohol and water would not be outside the framework of the invention. It should be noted that the quantity of this alcohol or polyalcohol, if it is present, is such that the polymer or copolymer is present in the form of a true solution.

Preparation of the spray can be carried out in several ways.

According to a first variant, the aqueous atomizing spray is obtained by mixing the phytosanitary formulation, which is diluted, emulsified or dispersed in an aqueous solution, with the anti-leaching agent which is present in solid form or in the form of a dispersion in a compound which is not a solvent of the polymer or copolymer.

According to this first variant, the quantity of water in the phytosanitary formulation is such that the anti-leaching agent is present, in the aqueous atomizing spray, in the form of an aqueous solution or dispersion having a polymer or copolymer concentration such that the viscosity of the anti-leaching agent is less than or equal to 10 times the viscosity of an aqueous polymer or copolymer solution free from reticulating agent, having the same concentration.

This variant illustrates a use of the anti-leaching agent as an additive (tank-mix). The anti-leaching agent is mixed with the phytosanitary formulation before the latter is applied to the plant to be treated.

The phytosanitary formulation which can be utilized, which will be described below, can be originally in the form of a powder, granules, a concentrated emulsion, solution or dispersion. Prior to being brought into contact with the anti-leaching agent, the phytosanitary formulation is diluted, emulsified, or dispersed, in an aqueous medium. Said medium is preferably water, but the possibility of adding any other common solvent or dispersant is not excluded.

The quantity of water mixed with the phytosanitary formulation depends on the concentration of active ingredient required for the application, and verification of the condition mentioned above, i.e. the fact that the anti-leaching agent is present, in the aqueous atomizing spray, in the form of an aqueous solution or dispersion having a (co)polymer concentration such that the viscosity of the anti-leaching agent is less than or equal to 10 times the viscosity of an aqueous (co)polymer solution free from reticulating agent, having the same concentration.

A first method of carrying out this first variant consists in utilizing the anti-leaching agent which is present in the form of a solid, more particularly in the form of a divided solid, such as a powder, for example.

The anti-leaching agent can be obtained, for example, by simply mixing the two constituents making up the anti-leaching agent.

The second method of carrying out this first variant consists in utilizing the anti-leaching agent in the form of a dispersion in a compound which is not a solvent of the polymer or copolymer.

More particularly, the compound which is not a solvent of the polymer or copolymer is selected throughout from oils of animal or vegetable origin, or from esters of fatty acids, or from hydrocarbonated oils. The oils of animal origin that may be mentioned include, amongst others, sperm whale, dolphin, whale, seal, sardine, herring, dogfish, and cod liver oil.

As examples of oils of vegetable origin, the following, amongst others, may be mentioned: rape-seed, sunflower, ground-nut, olive, walnut, maize, soya, linseed, hemp, grapeseed, copra, palm, cotton-seed, babassu, jojoba, sesame, castor and coriander oil. It is also possible to utilize saturated or non-saturated fatty acid esters, comprising, for the acid part, 6 to 40 carbon atoms, optionally carrying one or more hydroxylated groups. Examples of fatty acids that can be mentioned in particular include oleic, myristoleic, palmitoleic, petroselenic, erucic, linoleic, linolenic and ricinoleic acid. The methyl, ethyl and propyl esters of these acids are particularly suitable. More particularly, mention may be made of the products of alcoholysis, or to be more precise, methanolysis of the oils.

It is also possible to utilize aliphatic hydrocarbonated paraffin-type or aromatic oils (petroleum fractions etc.).

The content of this compound which is not a solvent of the (co)polymer varies widely. However, advantageously, it represents at least 50% by weight of the anti-leaching agent ((co)polymer/reticulating agent).

According to this possibility, the polymer or copolymer can be found in the form of solid particles.

The anti-leaching agent is advantageously obtained by simply mixing the different constituents in the necessary proportions.

According to a second variant, the aqueous atomizing spray is obtained by mixing the phytosanitary formulation with the anti-leaching agent; the latter being present in the form of an aqueous solution or dispersion having a polymer or copolymer concentration such that the viscosity of the anti-leaching viscosity is less than or equal to 10 times the viscosity of an aqueous polymer or copolymer solution free from reticulating agent, having the same concentration.

According to this second variant, the phytosanitary formulation present in the form of a powder, granules, or a concentrated emulsion, solution or dispersion, is mixed with a solution or dispersion of the anti-leaching agent.

There is nothing to prevent use of a phytosanitary formulation which has previously been diluted, emulsified or dispersed in an aqueous medium, as soon as the concentration of active ingredient in the resultant atomizing spray is sufficient.

According to this variant, the anti-leaching agent has a water content such that the polymer concentration and viscosity conditions indicated above are satisfactory.

This variant also illustrates a use of the anti-leaching agent as an additive (tank-mix).

A third variant consists in preparing the atomizing sprays by diluting, dispersing or emulsifying in an aqueous medium, the phytosanitary formulation free from water and containing the anti-leaching agent in solid form, or in the form of a dispersion in a compound which is not a solvent of the polymer or copolymer.

According to this third variant, the quantity of water is such that the anti-leaching agent, in the atomizing spray, is present in the form of an aqeuous solution or dispersion having a polymer or copolymer concentration such that the viscosity of the anti-leaching agent is less than or equal to 10 times the viscosity of an aqueous polymer or copolymer solution free from reticulating agent, having the same concentration.

According to a preferred method of carrying out this variant, the phytosanitary formulation is present in a solid form containing the anti-leaching agent in solid form.

The spray is thus obtained by mixing into the phytosanitary formulation containing the anti-leaching agent, a sufficient quantity of an aqueous medium, preferably water, in such a way that the above-mentioned (co)polymer concentration and viscosity conditions are verified.

This variant is representative of a use of the anti-leaching agent as a constituent of the phytosanitary formulation.

A first method of preparation of this kind of phytosanitary formulation consists of mixing all its constituents in the form of solids.

If necessary, the solid formulation obtained can be formed by granulation and/or extrusion, to provide granules.

A second method of preparation consists of preparing a solution or emulsion or dispersion in an aqueous medium, of the various constituents of the phytosanitary formulation, with the exception of one of the two constituents of the anti-leaching agent. This should preferably be the (co) polymer.

The resulting formulation is then dried.

The drying takes place using conventional means. However, said drying is preferably by atomization, i.e. by atomization of the suspension in a warm atmosphere (spray-drying). This warm atmosphere is, advantageously, air.

The atomization can be carried out using any atomizer known in itself, for example an atomizing nozzle of the watering-can rose type, or another type. "Turbine" atomizers can also be used.

A parallel-flow or counter-flow drying process can be used.

Out of the various atomizing techniques that can be utilized in the present procedure, reference may be made in particular to the basic work by MASTERS, entitled "SPRAY-DRYING" (second edition, 1976, George Godwin Editions, London).

It should be noted that use can also be made of the atomizing-drying operation using a "flash" reactor, for example of the type described in particular in the French patent applications nos. 2,257,326, 2,419,754 and 2,431,321.

By way of illustration, the gas inlet temperature during drying is between 150 and 250° C. Clearly, the temperature to which the active ingredient is subjected during drying remains below the degradation temperature of the constituents of said formulation.

If Once drying is completed, the formulation obtained is then mixed with the (co)polymer, in the conventional way.

It should be recalled that the phytosanitary formulations that can be utilized contain at least one phytosanitary active ingredient. This can be selected throughout from pesticides (herbicides, insecticides, fungicides etc.) or plant-growth control additives (oligo-elements).

More particularly, the content of phytosanitary active ingredient is such that the weight ratio of said active ingredient to anti-leaching agent is 0.1 to 50%.

The active ingredients included in the composition of such phytosanitary formulations may be solid, water-soluble or water-dispersible.

Examples of suitable active ingredients include, amongst others, Ametryne, Diuron, Linuron, Chlortoluron, Isoproturon, Nicosulfuron, Metamitron, Diazinon, Aclonifen, Atrazine, Chlorothalonil, Bromoxynil, Bromoxynil heptanoate, Bromoxynil octanoate, Mancozeb, Manebe, Zineb, Phenmedipham, Propanyl, the phenoxyphenoxy series, the heteroaryloxyphenoxy series, CMPP, MCPA, 2,4-D, Simazine, the active products of the imidazolinone series, the organophosphonate family, with, notably, Azinphos-ethyl, Azinphos-methyl, Alachlorine, Chlorpyriphos, Diclofop-methyl, Fenoxaprop-p-ethyl, Methoxychlorine, natural or synthetic pyrethroids, and Fenoxycarb. Aminophosphate derivatives and preferably glyphosate, sulphosate, glufosinate, and their organic salts (ammonium salts, which may or may not be substituted, of which the secondary or primary amines, such as isopropylamine or dimethylamine, or diamines such as ethylene diamine, or its sulfonium salts, in particular trimethyl sulfonium) or inorganic salts (such as alkaline metal salts such as sodium or potassium).

The active ingredient can likewise be selected throughout from mineral compounds of the metallic oxychloride type (such as copper for example).

The present invention is likewise suitable for the preparation of formulations comprising nutrients, such as, in particular, metallic salts such as zinc and iron, for example, and preferably manganese. These salts are used in the form of E.D.T.A.-type chelates for example, or sulphates.

The constituents of the phytosanitary formulations are those generally used in formulations in this field.

They therefore usually comprise surfactants whose role may be to stabilize an emulsion, a suspension, or a suspension-emulsion, to promote dispersion of the active ingredient, and to promote moistening with other constituents of the formulation.

Said surfactants may or may not be ionic.

The quantity of surfactant utilized depends on the form of the formulation. The expert can determine this without difficulty.

Examples of anionic surfactants are given in the following list, which is not intended to be exhaustive:

alkylsulphonic acids, arylsulphonic acids, optionally substituted by one or more hydrocarbon groups, and of which the acid function is partially or wholly salified, such as alkylsulphonic acids in $C_8$–$C_{50}$, more particularly in $C_8$–$C_{30}$, and preferably in $C_{10}$–$C_{22}$, benzenesulphonic acids, naphthalenesulphonic acids, substituted by one to three alkyl groups in $C_1$–$C_{30}$, preferably $C_4$–$C_{16}$, and/or alkenyl groups in $C_2$–$C_{30}$, and preferably in $C_4$–$C_{16}$, mono- or diesters of alkylsulphosuccinic acids, of which the alkyl part, which may be linear or branched, may optionally be substituted by one or more hydroxylated and/or alcoxylated groups, linear or branched in $C_2-C_4$ (preferably ethoxylated, propoxylated, or ethopropoxylated).

ester phosphates selected throughout more particularly from those comprising at least one saturated, non-saturated or aromatic, linear or branched hydrocarbonated group, comprising 8 to 40 carbon atoms, preferably 10 to 30, optionally substituted by at least one alcoxylated (ethoxylated, propoxylated, ethopropoxylated) group. In addition, they comprise at least one ester phosphate group, mono- or diesterified in such a way that there may be one or two free, or partially or wholly salified, acid groups. The preferred ester phosphates are of the type of the mono- and diesters of phosphoric acid, alcoxylated (ethoxylated and/or propoxylated) mono-, di- or tristyrylphenol, and alcoxylated (ethoxylated and/or propoxylated) mono-, di- or trialkylphenol, optionally substituted by one to four alkyl groups; of phosphoric acid and an alcoxylated (ethoxylated, or ethopropoxylated) alcohol in $C_8-C_{30}$, preferably in $C_8-C_{22}$; phosphoric acid and a non-alcoxylated alcohol in $C_8-C_{22}$, preferably in $C_{10}-C_{22}$;

ester sulphates obtained from saturated or aromatic alcohols, optionally substituted by one or more alcoxylated (ethoxylated, propoxylated or ethopropoxylated) groups, and for which the sulphate functions are present in the form of free, or partially or wholly neutralized acids. As examples, mention may be made of the ester sulphates obtained more particularly from saturated or non-saturated alcohols in $C_8-C_{20}$, optionally comprising 1 to 8 alcoxylated (ethoxylated, propoxylated or ethopropoxylated) units); the ester sulphates obtained from polyalcoxylated phenol, substituted by 1 to 3 saturated or non-saturated hydroxycarbonated groups in $C_2-C_{30}$, and in which the number of alcoxylated units is between 2 and 40; the ester sulphates obtained from polyalcoxylated mono-, di-, or tristyrylphenol in which the number of alcoxylated units varies from 2 to 40.

It should be noted that in cases where the compounds are in a partially or wholly salified form, the counter-ion may be an alkaline metal, such as sodium or potassium, or else an ammonium ion of the formula $N(R)_4+$, where R, which may be identical or different, represents a hydrogen atom or an alkyl radical in $C_1-C_4$, optionally substituted by an oxygen atom.

Examples of non-ionic surfactants are given in the following list, which is not exhaustive, by way of illustration:

polyalcoxylated (ethoxylated, propoxylated or ethopropoxylated) phenols substituted by at least one alkyl radical in $C_4-C_{20}$, preferably in $C_4-C_{12}$, or substituted by at least one alkylaryl radical, of which the alkyl part is in $C_1-C_6$. More particularly, the total number of alcoxylated units is between 2 and 100. By way of example, mention may be made of the polyalcoxylated mono-, di- or tri (phenylethyl) phenols, or the polyalcoxylated nonylphenols;

alcohols or fatty acids in $C_6-C_{22}$, optionally polyalcoxylated (ethoxylated, propoxylated or ethopropoxyslated). Should these be present, the number of alcoxylated units is between 1 and 60. The term "ethoxylated fatty acid" includes both the products obtained by ethoxylation of a fatty acid by ethylene oxide and those obtained by esterification of a fatty acid by a polyethylene glycol;

polyalcoxylated (ethoxylated, propoxylated or ethopropoxylated) triglycerides of plant or animal origin. Also suitable are triglycerides produced from lard, tallow, ground-nut oil, butter oil, cotton grain oil, linseed oil, olive oil, palm oil, grapeseed oil, fish oil, soya oil, castor oil, rape-seed oil, copra oil, coconut oil, and comprising a total number of alcoxylated units between 1 and 60. The term "ethoxylated triglyceride" refers to both the products obtained by ethoxylation of a triglyceride by ethylene oxide and those obtained by trans-esterification of a triglyceride by a polyethylene glycol;

esters of polyalcoxylated (ethoxylated, propoxylated or ethopropoxylated) sorbitan, more particularly esters of cyclized sorbitol of fatty acids from $C_{10}$ to $C_{20}$ such as lauric acid, stearic acid or oleic acid, and comprising a total number of alcoxylated units between 2 and 50.

The formulations may comprise other conventional additives used in this field, whose properties may include, amongst others, the roles of wetting agents, dispersants, disintegrating agents, binding agents, anti-caking agents, and/or stabilizers.

The quantity of these compounds varies widely, depending on the formation of the formulation.

Such compounds include, amongst others, salts of alkaline metals or of alkylnaphthalene ammonium sulphonates condensed in formol; salts of alkaline metals or of ammonium of 4,4'-dihydroxybiphenol sulphonate condensed in formol; salts of alkaline metals or ammonium of alkylarylphosphates or alkyarylsulphates, such as the polyoxyethylenated and/or polyoxypropylenated mono-, di- or tristyryl phenols which may be phosphated or sulphated, neutralized or not neutralized, and mixtures of these. It should be noted that ammonium represents $N(R)_4+$, with R, which may be identical or different, representing hydrogen atoms or hydrocarbonated radicals in $C_1-C_4$.

Also suitable are alkaline-metal or ammonium salts of polymers comprising at least one monomer selected throughout from the non-saturated acids, diacids or anhydrides in $C_3-C_5$, optionally combined with at least one monomer selected throughout from the linear or branched, non-saturated hydrocarbonated radicals in $C_4-C_8$.

More particularly, it is possible to use polymers comprising as monomers: malic acid, malic anhydride, acrylic acid, and methacrylic acid, alone or in mixtures. Said polymers can likewise comprise at least one monomer selected throughout from isobutylene or diisobytylene.

This polymer can be present in acid form or else in the form of an alkaline metal salt or ammonium salt. The copolymer is preferably found in the form of sodium salts. It is preferable to utilize a polymer comprising malic acid and/or malic anhydride combined with isobutylene and/or diisobutylene. The monomers are distributed alternately in the molecule. The proportion of the acid/anhydride-type monomer in relation to the hydrocarbonated-type monomer is preferably 50/50.

It is noted that the surfactants and agents just cited are different from the compounds included in the formulation as anti-leaching agent. The former do not have a molecular weight as great as that of the anti-rebound compounds utilized in the invention.

As an anti-caking agent, the following may be suitable: ammonium or sodium phosphates, sodium carbonate or bicarbonate, sodium acetate, sodium metasilicate, magnesium, zinc or calcium sulphate, magnesium hydroxide, calcium chloride, molecular sieves, barium or calcium oxide and silica, alone or in a mixture.

Of the chemical stabilizers, mention may be made, without intending to be restrictive, of alkaline-earth metal or transitional sulphates, sodium hexametaphosphate, calcium chloride, and boric anhydride, alone or in a mixture.

The formulations may, if necessary, comprise one or more inert charges, such as clays, synthetic or diatomaceous silicas, calcium or magnesium silicates, titanium dioxide, aluminium, zinc or calcium oxide, calcium or magnesium carbonate, sodium, ammonium or calcium sulphate, and carbon black, alone or in a mixture.

The quantity of charge, if present, can be determined without difficulty by the expert.

Preparation of the phytosanitary formulations not containing the anti-leaching agent is carried out using the conventional method in this field.

Thus, should the formulations be present in the form of solutions, suspensions or emulsions, the constituents of the formulation are brought into contact, including, if necessary, the conventional additives assisting in the formulation, such as, for example, anti-foaming agents (e.g. silicone substances).

The operation is generally carried out without agitation at a temperature close to the ambient temperature.

Should the formulation be present in the form of a powder, a drying stage is carried out after that of bringing the various constituents of the formulation into contact.

This drying takes place utilizing conventional means. A description of these has been given above, and will not be repeated here.

Should the phytosanitary formulation be present in solid form, the various constituents are generally mixed to obtain a solid or pasty mixture. This mixture can then be dried.

Finally, if necessary, the solid formulation obtained can be formed by granulation and/or extrusion, to give granules.

Concrete examples of the invention, which are not exhaustive, are given below.

EXAMPLES 50 g of mixtures whose composition is summarized in the following table are prepared:

| Example | 1 (reference) | 2 | 3 | 4 (reference) | 5 | 6 |
|---|---|---|---|---|---|---|
| Active ingredient (%) | 2 (1%) | 2 (1%) | 2 (1%) | 1 (1%) | 1 (1%) | 1 (1%) |
| Guar (a) | 0.1% | 0.1% | 0.1% | 0 | 0 | 0 |
| HP guar (b) | 0 | 0 | 0 | 0.1% | 0.1% | 0.1% |
| Zr lactate (c) | 0 | 0.044% | 0.044% | 0 | 0.044% | 0.044% |
| $CaCl_2$ (d) | 0 | 0 | 0.333% | 0 | 0 | 0.333% |

(a): Guar: Meyprogat ® 60 (average molar mass 500000 g/mol - marketed by Rhodia Meyhall) placed in a 1% solution in water having a pH adjusted to 5 with HCl (1M).
(b): HP guar: hydroxpropyl guar Jaguar ® 105 (average molar mass 500000 g/mol - marketed by Rhodia Meyhall) placed in a 1% solution in water having a pH adjusted to 5 with HCl (1M).
(c): Zr lactate: 29.7% solution of zirconium lactate - Rhodoline ® RHPN (marketed by Rhodia Chimie). The pH is adjusted to 5 by the addition of hydrochloric acid (1M). After adjustment of the pH, the content of dry ingredients is 15.4%.
(d): The hardness of the water is simulated by an addition of $Ca^{2+}$ ions equivalent to 300 ppm of $CaCO_3$: 0.17 g of $CaCl_2$ is dissolved in 9.83 g of water. This mixture is substitued for 10 g of purified water.

NB: The percentages in the table correspond to the weight of dry ingredient.

Formulae 1 and 2 are as follows:

| 1 | % | 2 | % |
|---|---|---|---|
| Mancozeb (fungicide) | 80 | Bordeaux spray | 77 |
| Borresperse (Borregard) (*) | 8 | Borresperse (Borregard) (*) | 12 |
| Supragil MNS/90 (Rhodia) (**) | 2 | Supragil MNS/90 (Rhodia) | 5 |
| Geropon SDS (Rhodia) (*) | 2 | () | |
| Argirec B/24 (BMP clay) | 8 | Rhodacal DS/10 (Rhodia) (***) | 2 |
| | | Prussian Blue | 2 |
| | | Bevaloid 6352DD (Bevaloid) | 2 |

(*) Na lignosulphate
(**) condensed methyl naphthalene
(***) Na dioctyl sulphosuccinate
(****) Na dodecyl bezenesulphonate The different constituents are mixed in the following order using magnetic agitation: water (or water+calcium ions), polymer, active ingredient then reticulating agent.

A homogeneous dispersion is obtained, whose appearance is identical to that of a preparation of active ingredient diluted in water.

The mixtures are dried for 24 hours in aluminium cupels in a ventilated oven at 50° C.

Part of the dry film is removed, weighed, then immersed in 300 ml of purified water (representing rainwater) and is left, under agitation (HEIDOLPH Promax 2020 agitating table, speed 3.5) for 30 hours.

The absorbency of the liquid in which the film is placed is measured with a METROHM Photometer 662 turbidimeter with a wavelength=630 nm. The equipment is calibrated using purified water (absorbency=0).

| Example | 1 (reference) | 2 | 3 | 4 (reference) | 5 | 6 |
|---|---|---|---|---|---|---|
| Absorbency | 7.6 | 0.5 | 0.4 | 8.5 | 0.4 | 0.8 |

The abosorbency value of the samples is divided by the mass of the dry film placed in each receptacle (to correct variations in concentration).

What is claimed is:

1. A method of preventing leaching of an active agent applied to a plant with an aqueous atomizing spray comprising a phytosanitary formulation comprising said active agent, said method comprising the steps of:
   a) spraying on the plant said aqueous atomizing spray comprising said phytosanitary formulation, and an anti-leaching agent comprising:
      at least one polyhydroxylated or polycarboxylated polymer or copolymer, and
      at least one reticulating agent comprising at least one metal selected from Columns IVA, IB and IIIB of the periodic table of the elements,
      said anti-leaching agent being present, in the aqueous atomizing spray, in the form of an aqueous solution or dispersion of the polymer or copolymer, with a polymer or copolymer concentration such that the viscosity of the anti-leaching agent is less than or equal to 10 times the viscosity of an aqueous polymer or copolymer solution free from reticulating agent, with the same concentration, and
   b) forming a gel by drying of the anti-leaching agent on the plant.

2. A method according to the claim 1, wherein the polymer or copolymer is a polyhydroxylated polymer or copolymer and is selected from the group consisting of polysaccharides of animal origin, polysaccharides of plant origin, polysaccharides of bacterial origin, polyvinyl alcohol, polyphenolic alcohols, derivatives of polyphenolic alcohols, and polyoxyalkylenated derivatives of glycol.

3. A method according to claim 1, wherein the polymer or copolymer is a polyhydroxylated polymer or copolymer and is selected from the group consisting of guar gum, its non-ionic derivatives, its anionic derivatives, its cationic derivatives, and its amphoteric derivatives.

4. A method according to claim 1, wherein the polymer or copolymer is selected from the group consisting of guar, alkylated derivatives of guar;

hydroxyalkyl guar wherein the alkyl group comprises from 2 to 4 carbon atoms, and is linear or branched, carboxymethyl guar, and carboxymethyl hydroxyalkyl guar wherein the alkyl group comprises from 2 to 4 carbon atoms, and is linear or branched.

5. A method according to claim 1, wherein the polymer or copolymer is a polycarboxylated polymer or copolymer, and is obtained from:

at least one saturated or unsaturated monomer comprising from 3 to 10 carbon atoms, and comprising one or more carboxylic group present in the form of an acid, or of alkaline metal salt, optionally, at least one hydrocarbonated monomer comprising one or more ethylenic unsaturation, and optionally, at least one monomer comprising an alkylene oxide group.

6. A method according to claim 1, wherein the polymer or copolymer has a molecular mass of between $10^4$ and $5.10^6$ g/mol.

7. A method according to claim 1, wherein the reticulating agent is a water-soluble, water-dispersible or emulsifiable compound, found in the form of:

organic derivatives selected from the group consisting of:
linear or branched, saturated or unsaturated, aliphatic, carboxylic acid salts, comprising from 2 to 18 carbon atoms, and optionally comprising one or more hydroxyl group, and aliphatic β-diketone or β-ketoester chelates, comprising from 5 to 10 carbon atoms, or comprising at least one aromatic group, or mineral derivatives selected from the group consisting of oxides, hydroxides, and mixtures thereof.

8. A method according to claim 1, wherein the metal is selected from the group consisting of zirconium, titanium, copper and aluminum.

9. A method according to claim 1, characterized in that a weight ratio of the reticulating agent and the polymer or copolymer of between 0.005 and 2.

10. A method according to claim 2, wherein the weight ratio is of between 0.01 and 0.5.

11. A method according to claim 1, wherein the aqueous atomizing spray is obtained by mixing a diluted, emulsified or dispersed, phytosanitary formulation in an aqueous medium, and an anti-leaching agent which is present in solid form, or in the form of a dispersion in a compound which is not a solvent of the polymer or copolymer, the quantity of water in the phytosanitary formulation being such that the anti-leaching agent is present, in the atomizing spray, in the form of an aqueous solution or dispersion having a polymer or copolymer concentration such that the viscosity of the anti-leaching agent is less than or equal to 10 times the viscosity of an aqueous polymer or copolymer solution free from reticulating agent, having the same concentration.

12. A method according to claim 11, characterized in that the compound which is not a solvent of the polymer or copolymer is selected from the group consisting of oils of animal or vegetal origin, esters of fatty acids, and hydrocarbonated oils.

13. A method according to claim 11, wherein the anti-leaching agent comprises at least 50% by weight of the compound which is not a solvent of the copolymer represents.

14. A method according to claim 1, wherein the aqueous atomizing spray is obtained by mixing the phytosanitary formulation with the anti-leaching agent, which is present in the form of an aqueous solution or dispersion having a polymer or copolymer concentration such that the viscosity of the anti-leaching agent is less than or equal to 10 times the viscosity of an aqueous polymer or copolymer solution free from reticulating agent, having the same concentration.

15. A method according to claim 14, wherein the phytosanitary formulation is in a diluted, emulsified or dispersed form in an aqueous medium.

16. A method according to claim 15, wherein the aqueous atomizing spray is obtained by diluting, in an aqueous medium, the phytosanitary formulation, free from water, and containing the anti-leaching agent in solid form or in the form of a dispersion in a compound which is not a solvent of the polymer or copolymer; the quantity of water being such that the anti-leaching agent, in the atomizing spray, is present in the form of an aqueous solution or dispersion, having a polymer or copolymer concentration such that the viscosity of the anti-leaching agent is less than or equal to 10 times the viscosity of an aqueous polymer or copolymer solution free from reticulating agent, having the same concentration.

17. A method according to claim 16, wherein the phytosanitary formulation is in solid form, comprising the anti-leaching agent in solid form.

18. A method according to claim 1, wherein the phytosanitary formulation comprises a phytosanitary active ingredient, the weight ratio of said active ingredient to anti-leaching agent being from 0.1 to 50%.

\* \* \* \* \*